US009295961B2

(12) United States Patent
Laska et al.

(10) Patent No.: US 9,295,961 B2
(45) Date of Patent: Mar. 29, 2016

(54) VARIOUS METHODS AND APPARATUSES FOR INTERNALLY HEATED RADIANT TUBES IN A CHEMICAL REACTOR

(75) Inventors: Timothy E. Laska, Loveland, OH (US); John T. Turner, West Chester, OH (US)

(73) Assignee: Sundrop Fuels, Inc., Longmont, CO (US)

( * ) Notice: Subject to any disclaimer, the term of this patent is extended or adjusted under 35 U.S.C. 154(b) by 750 days.

(21) Appl. No.: 13/429,752

(22) Filed: Mar. 26, 2012

(65) Prior Publication Data

US 2013/0247454 A1  Sep. 26, 2013

(51) Int. Cl.
*C10L 1/12* (2006.01)
*C10J 3/46* (2006.01)
(Continued)

(52) U.S. Cl.
CPC ............... *B01J 8/087* (2013.01); *B01J 8/0025* (2013.01); *B01J 8/12* (2013.01); *B01J 19/02* (2013.01); *C07C 2/00* (2013.01); *C07C 2/76* (2013.01); *C07C 5/327* (2013.01); *C10G 2/32* (2013.01); *C10G 9/20* (2013.01); *C10J 3/48* (2013.01); *C10J 3/485* (2013.01); *C10J 3/506* (2013.01); *C10L 1/12* (2013.01); *C10L 9/083* (2013.01); *B01J 2208/0084* (2013.01); *B01J 2208/00132* (2013.01); *B01J 2208/00504* (2013.01); *B01J 2208/00513* (2013.01); *B01J 2219/0263* (2013.01); *C10J 2300/0903* (2013.01); *C10J 2300/0906* (2013.01); *C10J 2300/0916* (2013.01); *C10J 2300/0976* (2013.01); *C10J 2300/1223* (2013.01); *C10J 2300/1246* (2013.01); *C10J 2300/1665* (2013.01); *C10J 2300/1853* (2013.01); *Y02E 50/15* (2013.01); *Y02E 50/18* (2013.01); *Y02E 50/32* (2013.01); *Y02P 20/145* (2015.11)

(58) Field of Classification Search
USPC ........... 422/162, 623, 659; 44/457; 48/197 R; 585/501, 510, 700, 701
See application file for complete search history.

(56) References Cited

U.S. PATENT DOCUMENTS 4,971,600 A  11/1990  Baumann et al.
6,402,988 B1  6/2002  Gottzmann et al.
(Continued)

FOREIGN PATENT DOCUMENTS

WO  WO 2011/139199 A1  11/2011
WO  WO 2011/155962 A1  12/2011

OTHER PUBLICATIONS

International Search Report and Written Opinion, International Patent Application No. PCT/US2013/033773, dated Jun. 18, 2013, 15 pages. International Searching Authority/US, Alexandria, Virginia, USA.
(Continued)

*Primary Examiner* — Ellen McAvoy
*Assistant Examiner* — Chantel Graham
(74) *Attorney, Agent, or Firm* — Rutan & Tucker, LLP

(57) ABSTRACT

A radiant heat chemical reactor is configured to generate chemical products including synthesis gas products. Two or more tubes in the radiant heat chemical reactor separate an exothermic heat source, such as flames and gas from a regenerative burner, from the endothermic reaction of the reactant gas occurring within the cavity of the refractory vessel. The exothermic heat source heats a space inside the tubes. One or more feed lines supply chemical reactants to the cavity area between an inner wall of the cavity of the refractory vessel of the chemical reactor and the two or more tubes that are internally heated located with the cavity.

15 Claims, 10 Drawing Sheets

(51) Int. Cl.

| | | |
|---|---|---|
| *C07C 2/76* | (2006.01) | |
| *B01J 8/06* | (2006.01) | |
| *C07C 2/00* | (2006.01) | |
| *B01J 8/08* | (2006.01) | |
| *C10J 3/48* | (2006.01) | |
| *C10J 3/50* | (2006.01) | |
| *C10L 9/08* | (2006.01) | |
| *C10G 2/00* | (2006.01) | |
| *C10G 9/20* | (2006.01) | |
| *B01J 8/12* | (2006.01) | |
| *B01J 19/02* | (2006.01) | |
| *B01J 8/00* | (2006.01) | |
| *C07C 5/327* | (2006.01) | |

(56) References Cited

U.S. PATENT DOCUMENTS

| | | |
|---|---|---|
| 6,872,378 B2 | 3/2005 | Weimer et al. |
| 7,033,570 B2 | 4/2006 | Weimer et al. |
| 7,553,476 B2 | 6/2009 | Marrella et al. |
| 7,632,476 B2 | 12/2009 | Shah et al. |
| 7,686,856 B2 | 3/2010 | Hemmings et al. |
| 7,856,829 B2 | 12/2010 | Shah et al. |
| 7,871,457 B2 | 1/2011 | Shah et al. |
| 7,881,825 B2 | 2/2011 | Esposito et al. |
| 7,931,888 B2 | 4/2011 | Drnevich et al. |
| 7,985,399 B2 | 7/2011 | Drnevich et al. |
| 8,007,761 B2 | 8/2011 | Drnevich et al. |
| 9,011,560 B2 | 4/2015 | Simmons et al. |
| 2003/0182861 A1 | 10/2003 | Weimer et al. |
| 2003/0208959 A1 | 11/2003 | Weimer et al. |
| 2004/0219079 A1 | 11/2004 | Hagen et al. |
| 2005/0142049 A1 | 6/2005 | Amsden et al. |
| 2006/0140848 A1 | 6/2006 | Weimer et al. |
| 2006/0188433 A1 | 8/2006 | Weimer et al. |
| 2006/0199127 A1 | 9/2006 | Butler |
| 2007/0054227 A1 | 3/2007 | Tada et al. |
| 2007/0098602 A1 | 5/2007 | Haueter et al. |
| 2008/0025884 A1 | 1/2008 | Tonkovich et al. |
| 2008/0086946 A1 | 4/2008 | Weimer et al. |
| 2008/0222955 A1 | 9/2008 | Jancker et al. |
| 2009/0013601 A1 | 1/2009 | Mandich et al. |
| 2009/0313886 A1 | 12/2009 | Hinman |
| 2010/0000874 A1 | 1/2010 | Hinman |
| 2010/0137459 A1 | 6/2010 | Stites et al. |
| 2010/0270505 A1 | 10/2010 | Gallaspy et al. |
| 2010/0273899 A1 | 10/2010 | Winter |
| 2011/0107661 A1 | 5/2011 | Tirmizi et al. |
| 2011/0124927 A1 | 5/2011 | Stites et al. |
| 2011/0155958 A1 | 6/2011 | Winter et al. |
| 2012/0181483 A1 | 7/2012 | Simmons |
| 2012/0241677 A1 | 9/2012 | Perkins |

OTHER PUBLICATIONS

Notification Concerning Transmittal of International Preliminary Report on Patentability for International Application No. PCT/US2010/059564, mailed Dec. 20, 2012, 10 pages, The International Bureau of WIPO, Geneva, Switzerland.

Bridgwater, et al., "Fast Pyrolysis Processes for Biomass" Renewable and Sustainable Energy Reviews, vol. 4, No. 1, pp. 1-73, Mar. 2000.

Lede, "Solar Thermochemical Conversion of Biomass", Solar Energy, vol. 65, No. 1, 11 pages, Jan. 1, 1999.

Non-Final Rejection Action for U.S. Patent & Trademark Office, U.S. Appl. No. 13/254,020 mailed May 9, 2013, 21 pages. U.S. Patent & Trademark Office, Alexandria, Virginia USA.

Restriction Action for U.S. Patent & Trademark Office, U.S. Appl. No. 13/254,020 mailed Nov. 26, 2012, 6 pages. U.S. Patent & Trademark Office, Alexandria, Virginia USA.

International Search Report and Written Opinion, International Patent Application No. PCT/US 10/59564, dated Mar. 2, 2011, 12 pages. International Searching Authority/US, Alexandria, Virginia, USA.

Notice of Allowance for U.S. Appl. No. 13/254,020 mailed Dec. 3, 2014 7 pages.

Advisory Action for U.S. Appl. No. 13/254,020 mailed Mar. 17, 2014, 4 pages.

Non-Final Office Action for U.S. Appl. No. 13/254,020 mailed Jun. 16, 2014 28 pages.

Final Office Action for U.S. Appl. No. 13/254,020 mailed Oct. 29, 2013, 23 pages.

First Office Action for Chinese Patent Application No. 201080067327.0 mailed Aug. 5, 2014, 15 pages. State Intellectual Property Office of China.

Second Office Action for Chinese Patent Application No. 201080067327.0 mailed Feb. 2, 2015, 4 pages. State Intellectual Property Office of China.

Higuchi, Takayoshi "Steam Explosion of Wood", Sections 1-4, Biomass Handbook, © 1989 by OPA (Amsterdam), pp. 470-473 plus Cover, Biblio, Table of Contents excerpt. 7 pages total, Editors: Osamu Kitani & Carl W. Hall, ISBN 2-88124-269-3, Gordon and Breach Science Publishers S. A., Cooper Station, New York, New York.

"StakeTech—First Pulping System Receives Full Acceptance", May 14, 1996, 2 pages. Publisher: Business Wire. downloaded from http://www.thefreelibrary.com/StakeTech.

McCallum, Don, "Medium Density Fiber Board" pp. 8-11, Nov. 1, 1996 http://fennerschool-associated.anu.edu.au/fpt/mdf/manufacture.html.

```
                            ┌─────────┐
                            │  Cont.  │
                            └────┬────┘
                                 ▼
```

In step 525, an amount of heat flux generated at a given stage is controlled by 1) varying a physical depth of an internal heating of the radiant tube (or at least the length of the flame inside the tube) passing through that stage, 2) a rate amount of internal heat provided within each radiant tube in that stage, 3) an amount of tubes actively heating within that stage and thus tubes idling, and 4) any combination of the three.

In step 530, an amount of flames and heated gas from natural gas fired regenerative burners is supplied from at least both ends of the radiant tubes at temperatures between 900° C and 1800° C.

In step 535, maintaining an environmental pressure within the refractory vessel with one or more tight seals made out of 1) metal or 2) a welded seal between the radiant tubes that are internally heated and the refractory lined vessel, where the tight seals are designed to accommodate a differential thermal expansion of the radiant tubes and the refractory lined vessel are potentially made out of different materials which can affect the seal process at upper end temperatures, and the radiant tubes have a 1400°C-1800°C surface temperatures and the vessel inner cavity operates at temperatures between 900 C and 1600 C.

In step 540, the heating of the exothermic heat source and a feed rate of chemical reactants into the cavity of the chemical reactor is controlled in order to maintain the temperatures above 900° C in order to cause a rapid gasification reaction of dispersed falling biomass particulates and reactant gas to produce a resultant stable ash formation, complete amelioration of tar to less than 500 milligrams per normal cubic meter, and the production of the hydrogen and carbon monoxide products.

In step 545, synthesis product gases exit from the chemical reaction of the reactant gas and biomass particles from the radiant heat chemical reactor. A liquid fuel is generated from the synthesis product gases from the radiant heat chemical reactor.

```
                            ┌─────────┐
                            │   End   │
                            └─────────┘
```

Figure 5b

VARIOUS METHODS AND APPARATUSES FOR INTERNALLY HEATED RADIANT TUBES IN A CHEMICAL REACTOR

FIELD

The invention generally relates to radiant heat driven chemical reactors and in an embodiment specifically to reactors with tubes that are internally heated.

BACKGROUND

A radiant heat driven chemical reactor can be used to drive a number of processes including a process to generate syngas. Some prior art describes a detailed model for radiation to particulates and then convective heat transport from the particulates to the gas in a single tube reactor. This system uses a fluid-wall around the reacting particles to avoid build up and use an electrical heater located within the plenum of the reactor to heat everything.

SUMMARY

In an embodiment, a radiant heat driven chemical reactor can be used to drive a number of processes including a process to generate syngas. In an embodiment, one or more feed lines are configured to supply chemical reactants including 1) biomass particles, 2) reactant gas, 3) steam; 4) heat transfer aid particles, or 5) any of the four into the radiant heat chemical reactor. The indirect radiation driven geometry of the radiant heat chemical reactor uses radiation as a primary mode of heat transfer the reactant gas and any particles entrained with the gas. Each radiant tube separates an exothermic heat source, such as flames and gas from a regenerative burner, from the endothermic reaction of the reactant gas occurring within the cavity of the refractory vessel. The exothermic heat source heats a space inside the radiant tubes. The one or more feed lines supply the chemical reactants to the cavity area between an inner wall of the cavity of the refractory lined vessel and the one or more radiant tubes that are internally heated. The radiant tubes that are internally heated decrease tube failure issues because a heating gradient for each tube expands the solid material of the tube while a higher pressure environment within the refractory vessel compresses the walls of each tube, which contain the higher temperature of the gradient but a lower pressure environment. The radiation is absorbed by any heat-transfer-aid particles and any biomass particles present, and the heat is then transferred by conduction to the reacting gas at temperatures between 900° C. and 1600° C.

BRIEF DESCRIPTION OF THE DRAWINGS

The multiple drawings refer to the example embodiments of the invention.

FIGS. 5a-5b illustrate a flow diagram of an embodiment for a method to generate a synthesis product gas from a radiant heat driven chemical reactor.

Figure 1:
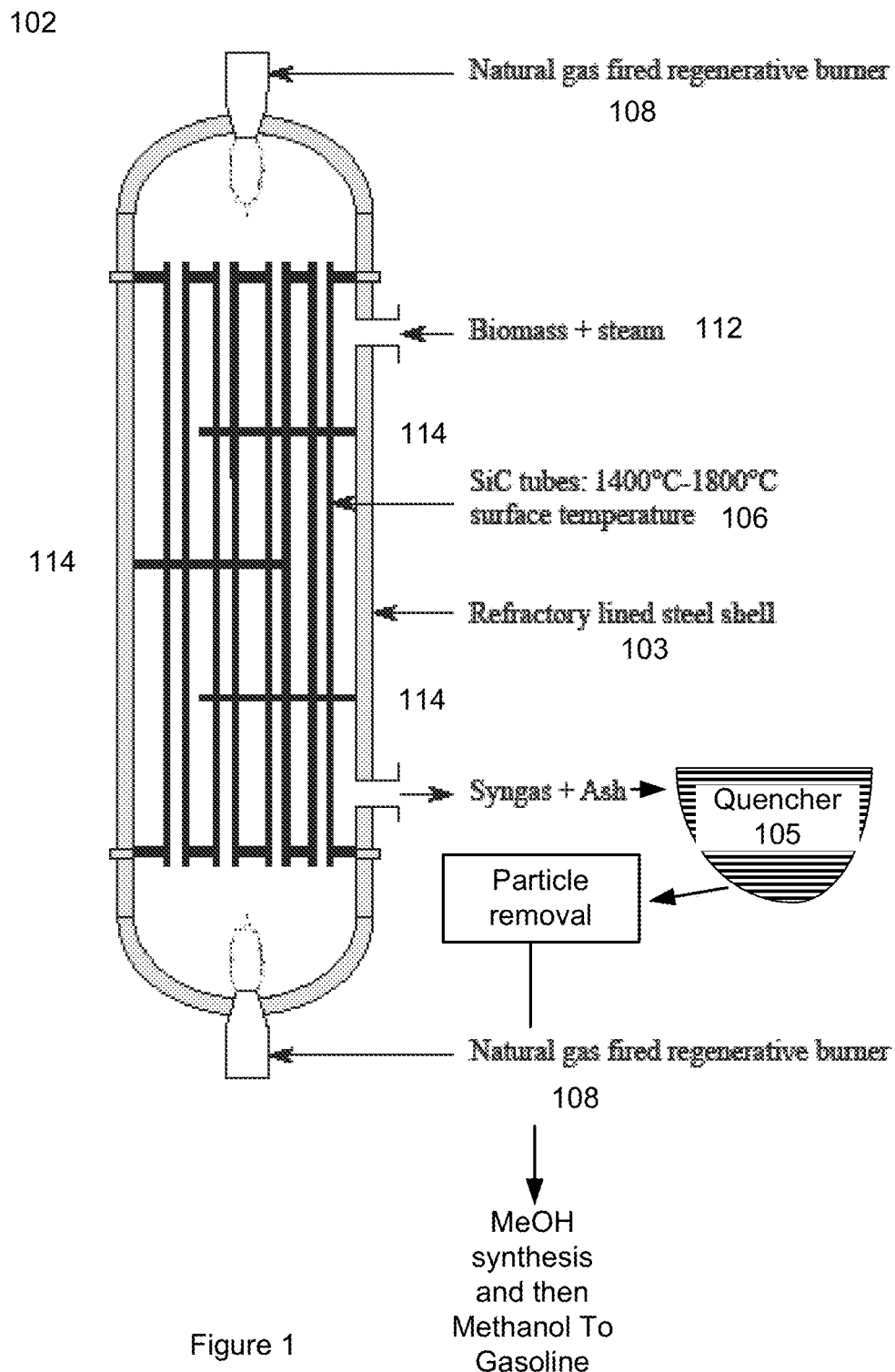
FIG. 1 illustrates a flow schematic of an embodiment for the radiant heat chemical reactor configured to generate chemical products including synthesis gas products.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific chemicals, named components, connections, types of heat sources, etc., in order to provide a thorough understanding of the present invention. It will be apparent, however, to one skilled in the art that the present invention may be practiced without these specific details. In other instances, well known components or methods have not been described in detail but rather in a block diagram in order to avoid unnecessarily obscuring the present invention. Thus, the specific details set forth are merely exemplary. The specific details may be varied from and still be contemplated to be within the spirit and scope of the present invention.

In general, a number of example processes for and apparatuses associated with a radiant heat driven chemical reactor and its associated integrated chemical plant are described. The following drawings and text describe various example implementations of the radiant heat chemical reactor's design. Also, several example chemical reactions designed to be conducted in the chemical reactor are also discussed but mainly a biomass gasification reaction will be used to illustrate the radiant heat chemical reactor's properties. Also example sources of the radiant heat for the reactor may be one or more of 1) solar energy, 2) gas-fired regenerative burners, 3) nuclear power, 4) electric heaters and 5) any combination of these four. For example, the endothermic chemical reaction(s) conducted in the chemical reactor includes one or more of the following: biomass gasification, steam methane reforming, methane cracking, a dry reforming reaction, steam methane cracking to produce ethylene, and various combinations of these reactions, to be conducted in this chemical reactor using primarily the radiant heat energy. Two or more tubes in the radiant heat chemical reactor separate an exothermic heat source from an endothermic reaction of reactant gas and biomass particles occurring within a cavity of the refractory vessel of the chemical reactor. The exothermic heat source heats a space inside the tubes. The tubes are located within the refractory vessel. One or more feed lines supply the reactant gas and biomass particles to the cavity area between an inner wall of the cavity of the refractory vessel and an outside wall of each of the two or more tubes that are internally heated. One skilled in the art will understand parts and aspects of many of the designs discussed below within this illustrative document may be used as stand-alone concepts or in combination with each other.

FIG. 1 illustrates a flow schematic of an embodiment for the radiant heat chemical reactor configured to generate chemical products including synthesis gas products. The multiple shell radiant heat chemical reactor 102 includes a refractory vessel 103 having an annulus shaped cavity with an inner wall. The radiant heat chemical reactor 102 has two or more radiant tubes 106 made out of a solid material. The one or more radiant tubes 106 are located inside the cavity of the refractory lined vessel 103.

The exothermic heat source 108 heats a space inside the tubes 106. Thus, each radiant tube 106 is heated from the inside with an exothermic heat source 108, such as regenerative burners, at each end of the tube 106. Each radiant tube 106 is heated from the inside with fire and gases from the regenerative burners through heat insertion inlets at each end of the tube 106 and potentially by one or more heat insertion ports located in between the two ends. Flames and heated gas of one or more natural gas fired regenerative burners 108 act as the exothermic heat source supplied to the multiple radiant tubes at temperatures between 900° C. and 1800° C. and connect to both ends of the radiant tubes 106. Each tube 106 may be made of SiC or other similar material.

One or more feed lines 112 supply biomass and reactant gas into the top or upper portion of the chemical reactor 102. The feed lines 112 for the biomass particles and steam enter below the entry points in the refractory lined vessel 103 for the radiant tubes 106 that are internally heated. The feed lines 112 are configured to supply chemical reactants including 1) biomass particles, 2) reactant gas, 3) steam, 4) heat transfer aid particles, or 5) any of the four into the radiant heat chemical reactor. A chemical reaction driven by radiant heat occurs outside the multiple radiant tubes 106 with internal fires. The chemical reaction driven by radiant heat occurs within an inner wall of a cavity of the refractory lined vessel 103 and an outer wall of each of the one or more radiant tubes 106.

The chemical reaction may be an endothermic reaction including one or more of 1) biomass gasification ($CnHm+H_2O \rightarrow CO+H_2+H_2O+X$), 2) steam methane reforming ($CH_4+H_2O \rightarrow CO+3H_2$), 3) steam methane cracking to produce ethane ($H_2O+CH_3+CH_3 \rightarrow C_2H_6+H_2O$), and 4) steam methane cracking to produce ethylene ($CH_4+H_2O \rightarrow C_2H_4$), and other similar hydrocarbon decomposition reactions, which are conducted in the radiant heat chemical reactor 102 using the radiant heat. A steam ($H_2O$) to carbon molar ratio is in the range of 1:1 to 1:4, and the temperature is high enough that the chemical reaction occurs without the presence of a catalyst.

Thus, each radiant tube 106 separates the exothermic heat source 108 from the endothermic reaction of the reactant gas (including biomass gasification) occurring within the cavity of the refractory vessel 103. The one or more feed lines 112 supply the chemical reactants to the cavity area between an inner wall of the cavity of the refractory vessel 103. Fire is inside the one or more tubes 106 and biomass, steam, natural gas and/or other chemical reactants flow outside the tubes 106 but within the outer shell/refractory vessel 103.

The gas-fired regenerative burners 108 supply heat energy to the chemical reactor 102 to aid in causing the radiant heat driven chemical reactor to have a high heat flux. The inside surfaces of the chemical reactor 102 are aligned to 1) absorb and re-emit radiant energy, 2) highly reflect radiant energy, and 3) any combination of these, to maintain an operational temperature of the enclosed ultra-high heat flux chemical reactor 102. Thus, the inner wall of the cavity of the refractory vessel 103 and the outer wall of each of the one or more tubes 106 emits radiant heat energy to, for example, the biomass particles and any other heat-transfer-aid particles present falling between an outside wall of a given tube 106 and an inner wall of the refractory vessel 103. The refractory vessel 103 thus absorbs or reflects, via the tubes 106, the concentrated energy from the regenerative burners 108 positioned along on the top and bottom of the refractory vessel 103 to cause energy transport by thermal radiation and reflection to generally convey that heat flux to the biomass particles, heat transfer aid particles and reactant gas inside the chemical reactor. The inner wall of the cavity of the thermal refractory vessel 103 and the multiple tubes 106 act as radiation distributors by either absorbing radiation and re-radiating it to the heat-transfer-aid particles or reflecting the incident radiation to the heat-transfer-aid particles.

The indirect radiation driven geometry of the radiant heat chemical reactor 102 uses radiation as a primary mode of heat transfer to the heat-transfer-aid particles, the reactant gas, and any biomass particles entrained with the heat-transfer-aid particles. The radiation is absorbed by the heat-transfer-aid particles, and the heat is then transferred by conduction to the reacting gas and any biomass particles present at temperatures between 900° C. and 1600° C. The heat-transfer-aid particles may be mixed with the reactant gas in the radiant heat chemical reactor 102 to sustain the reaction temperature and heat transfer rate to stay within a pyrolysis regime. The radiant heat chemical reactor 102 uses an ultra-high heat flux and high temperature that is driven primarily by radiative heat transfer, and not convection or conduction. A relatively constant heat flux is maintained during operation while any particles and reactant gas are introduced into the annular space between the tubes 106 and the refractory lined walls 103. Also, use of multiple radiant tubes 106 significantly increases radiant heat transfer surface area compared to just one central tube.

An inner wall of the refractory vessel 103 cavity and the radiant tubes 106 may be made of materials to allow them to be operated at high, >1200 degrees C., wall temperatures to enable the high heat transfer rates, rapid reaction kinetics of the very short residence time, and high selectivity of carbon monoxide and hydrogen produced from the gasification reaction for syngas. Optionally, the tubes 106 and walls are coated/lined with such materials as well.

Rather than using a complex configuration (microchannels, very small diameter tubes 106, etc.) for increasing convective surface area, the reactor 102 can use a very large cavity space and allow the large surface area to volume ratio of the particles flowing within the cavity to improve convection heat transfer to gas phase reactants. The particles act as direct absorbers, effectively increasing the emissivity of the particle-laden gas stream.

The radiant tubes 106 that are internally heated decrease tube failure issues because a heating gradient for each tube expands the solid material of the tube while a higher-pressure environment within the refractory vessel 103 compresses the walls of each tube. Each tube 106 internally contains the higher temperature of the heat gradient but a lower pressure environment causing the compression. Accordingly, the internally heated radiant tubes 106 have no pressure code issues when using a standard SiC tube. The temperature gradient across the tube wall is highest in the interior wall and lowest on the outer wall, which emits the radiant energy. Internally heated SiC radiant tubes 106 have more efficient heating to obtain radiant emissions due to a significantly reduced heated volume compared to an entire cavity space. The internally heated SiC radiant tubes 106 can have larger diameters than exterior heated radiant tubes 106 and thus lower capital cost due to need for fewer radiant tubes 106, potentially shorter radiant tubes 106, and fewer biomass or other chemical reactant feed point(s), all which increase capital saving.

The internal firing and heating of the radiant tubes 106 also decrease stress failures of the SiC radiant tube during operation due to thermal shock minimization at the full design temperature range of 900-1800° C. In addition to reducing thermal shock of the SiC tube, the internally fired and heated radiant tubes 106 can reduce the number of radiant tubes 106 significantly (possibly 10:1 or 15:1) needed to heat a given amount of biomass compared to an externally heated tube containing the biomass, as well as the number of biomass feed entry points into the vessel. The internally fired and heated radiant tubes 106 allow significant reductions in a physical size of the radiant heat chemical reactor. The internally fired and heated radiant tubes 106 allow a modular design that would enable full-scale demonstration with a single tube unit, and scaling by addition of modules. The internally fired and heated radiant tubes 106 give net benefits of lower capital cost, reduced operating cost, and improved reliability. The internal fired radiant heat chemical radiant tube design solves some feed issues because the particles flow outside the radiant tubes 106, solves some tube failure issues because it also decreases an amount of thermal shock due to the high heat flux with biomass loading, and solves some pressure concerns with using SiC at high temperatures.

The internally heated radiant tubes 106 are vertically orientated and have entry points at or near the top of the refractory vessel 103 as well as entry points at or near the bottom of the refractory vessel 103. The natural gas fired regenerative burners 108 connect to both ends of the tubes to supply heated gases and flames to the two or more SiC radiant tubes 106. At least two or more sets of regenerative burners 108 connect to the tubes 106, at least one set of regenerative burners 108 per end. The feed lines 112 for the biomass and steam enter in the upper portion of vessel.

The radiant heat chemical reactor 102 may be made up of multiple discrete stages in which the chemical reaction occurs within the refractory vessel 103 of the reactor. The refractory lined vessel is configured to have stages potentially divided by physical barrier surfaces 114 to increase residence time of the biomass particles and reactant gas within the refractory vessel 103 by not just falling straight through the vessel and instead an internal geometry of the vessel defined by the physical barrier surfaces 114 causes the biomass particles and reactant gas to travel a non-linear path through the vessel. The amount of heat flux generated at a given stage is controlled by 1) varying a physical depth of an internal heating of the radiant tube (or at least the length of the flame inside the tube) passing through that stage, 2) a rate amount of internal heat provided within each radiant tube in that stage, 3) an amount of tubes 106 actively heating within that stage and thus idling some tubes 106, and 4) any combination of the three. The stages allow benefits including fewer radiant tubes 106, potentially shorter radiant tubes 106 or different length radiant tubes 106 in each stage to shape radiant flux in that stage, and fewer biomass feed points such as a single point on top or one point on each side of the upper portion of the refractory vessel 103. The stages also allow modular grouping of radiant tubes 106. After transiting through the multiple stages of radiant heat flux within radiant heat chemical reactor, syngas and ash product exit near the bottom of the refractory vessel 103.

Note, the heat-transfer-aid particles may chemically inert to the chemical reaction occurring within the chemical reactor, are formed of solid state of matter versus a gaseous state or a liquid state, and may have an average effective diameter size of the heat-transfer-aid particles between 1,000,000 nanometers and 10,000 nanometers to produce a sufficient heat surface-area to mass ratio of these particles when dispersed with the reactant gas to stay within a pyrolysis regime during the chemical reaction.

In an embodiment, particles of biomass are gasified in the presence of a steam ($H_2O$) (steam biomass gasification reaction) and when a NG carrier gas is used then a simultaneous steam reformation of the methane ($CH_4$) occurs within the same reactor to produce reaction products that include hydrogen and carbon monoxide gas using the ultra-high heat flux thermal energy radiated from the inner wall of the cavity and from the multiple radiant tubes 106.

After the reaction in the chemical reactor 102 occurs, then rapid cooling occurs to capture the reaction products. A quench zone 105 is located immediately downstream of an exit of the chemical reactor 102 to immediately quench via rapid cooling the chemical reaction products including any hydrogen molecules, carbon monoxide molecules, and the ash and heat transfer aid particles exiting the chemical reactor 102. This achieves within 10 seconds a temperature after quenching of 800 degrees C. or less, which is below a level to reduce coalescence of ash remnants of the biomass particles. At the exit of the gasification reaction zone in the radiant tubes 106 of the chemical reactor 102, two or more tubes 106 form into a group at the exit and that group combines their reaction products and un-reacted particles from the biomass gasification into a larger pipe per group that forms a portion of the quench zone. One or more sprayers inside the larger pipe inject a cooling fluid directly into the reaction product syngas stream to make the temperature transition from the at least 900 degree C. exit temperature to less than the 800 degrees C. within the 0.1~10 seconds to prevent metal dusting corrosion of the pipe walls.

One or more hot particle filters 115 may remove particulates from the syngas stream exiting the quench zone 105, where the particulates are sent to an ash-holding vessel. Thus, a separator 115 coupled downstream of the radiant heat chemical reactor 102 separates out the heat-transfer-aid particles from gas products from the chemical reaction. The heat aid particle storage mechanism is configured to accumulate the heat-transfer-aid particles and any ash remnants of the biomass from the biomass gasification reaction that exit the chemical reactor. The separator 115 stores these particles and any ash remnants to extract their heat in order to heat a working fluid that drives an electricity generation apparatus, a steam generation unit, or other apparatus used in doing heat based processes. The products from the chemical reaction are supplied to a downstream chemical synthesis plant and potentially to a further on-site a gasoline synthesis plant.

A boiler steam supply may provide steam to the radiant heat chemical reactor 102 and make up at least part of the reactant gas supplied to the reactor. The heated working fluid from the heat aid storage mechanism 111 may be used in the boiler to generate the steam.

A control system (also see FIG. 8 for example) may be configured to control at least the heat-transfer-aid particle feed rate, the reactive gas (e.g. $CH_4$, Steam) feed rate, and an exit temperature out of the radiant heat chemical reactor 102 based on and sensor measurements of these parameters conveyed back to the control system.

Each set of regenerative burners 108 controlled by the control system may work as follows. Regeneration uses a pair of burners 108, which cycle to alternately heat the combustion air or recover and store the heat from the furnace exhaust gases. When one regenerative burner is firing, the other is exhausting the furnace gases. Exhaust gases pass through the regenerative burner body and into a media case, which contains refractory material. The refractory media is heated by the exhaust gases, thus recovering and storing energy from the flue products. When the media bed is fully heated, the regenerative burner currently firing is turned off and begins to exhaust the flue products. The regenerative burner with the hot media bed begins firing. Combustion air passes through the media bed and is heated by the hot refractory. Air preheat temperatures within 300 degrees F. to 500 degrees F. of the furnace temperature may be achieved resulting in exceptionally high thermal efficiency.

The heat-transfer-aid particles can also mitigate soot formation along with CO2 formation. The heat-transfer-aid particles allows coupling of radiant energy into gas chemistries, allowing operation in thermal, non-catalytic temperature regime and with lower area/capital cost, higher equilibrium conversions, looser control requirements, and lower operating costs. Heat-transfer-aids as additives may also include 1) chemicals that react to form small solid, heat-transfer-aid particles such as metal oxides, and 2) complex hydrocarbons that break apart during the reaction.

Generally, the operational temperature of the high heat flux driven chemical reactor is maintained at greater than 900 degrees C. and up above 1100 to 1600 degrees C. in most cases. The values of heat flux at these operating temperatures are high in this design. For example, convection biomass gasifiers used generally on coal particles typically at most reach heat fluxes of 5-10 kW/m^2. The high radiant heat flux biomass gasifier will use heat fluxes significantly greater, at least three times the amount, than those found in convection driven biomass gasifiers (i.e. greater than 25 kW/m^2). Generally, using radiation at high temperature (>950 degrees C. wall temperature), much higher fluxes (high heat fluxes greater than 80 kW/m^2) can be achieved with the properly designed reactor. In some instances, the high heat fluxes can be 100 kW/m^2-250 kW/m^2.

The control system can be configured to maintain the temperature of the chemical reactor to be above 1200 degrees C. in order to eliminate methane and C2+ hydrocarbons from the products exiting the radiant heat chemical reactor. Note, by feeding $CH_4$ (which does not react as $CH_4 \rightarrow C + 2H_2$ until ~1200°), a much higher heat load can be placed on the process at high temperature.

Figure 2:
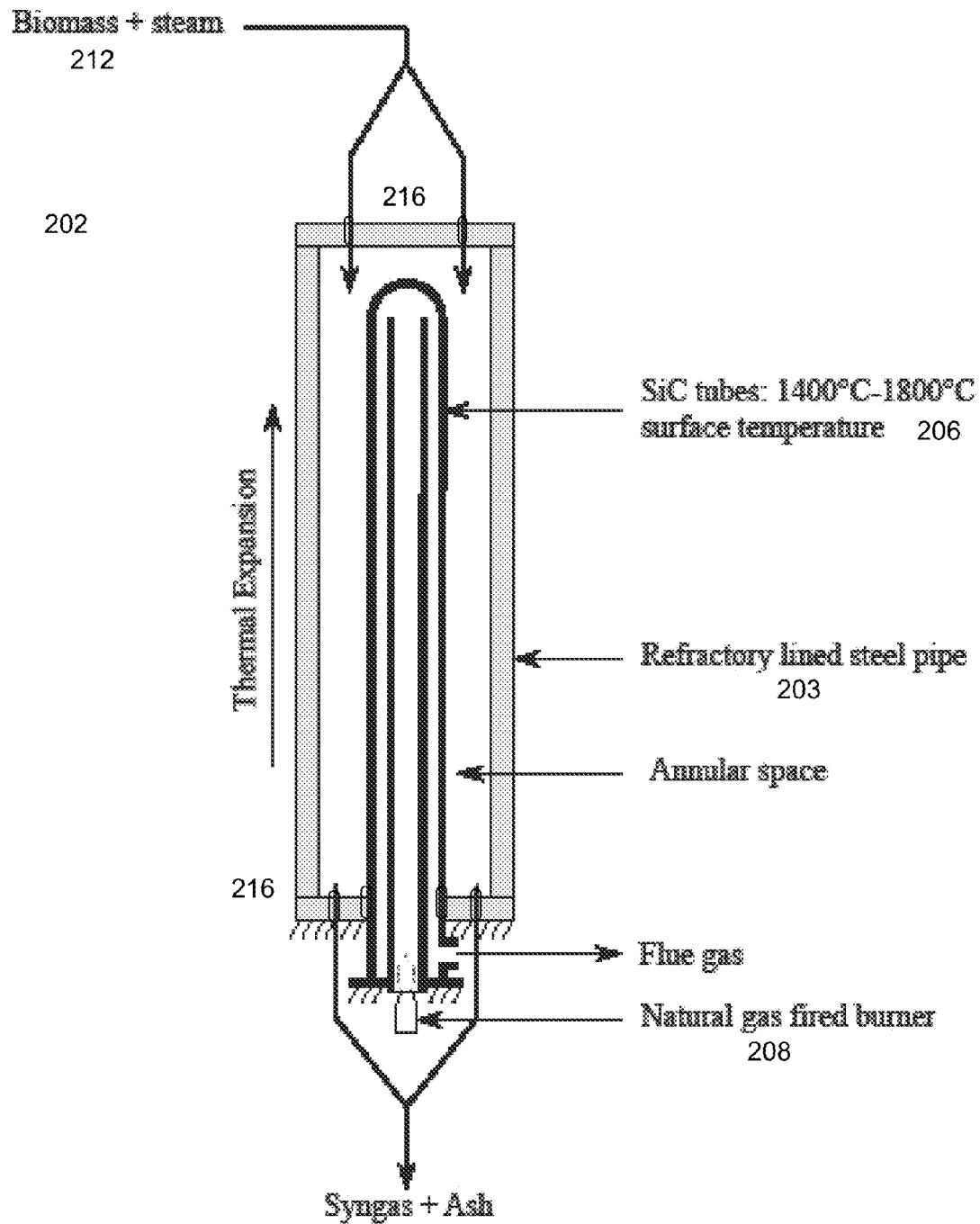
FIG. 2 illustrates a flow schematic of an embodiment for the radiant heat chemical reactor configured to generate chemical products including synthesis gas products.

FIG. 2 illustrates a flow schematic of an embodiment for the radiant heat chemical reactor configured to generate chemical products including synthesis gas products.

The chemical reactor 202 may have one or more internally heated radiant tubes 206 that are vertically orientated and but merely have entry points at or near the bottom of the refractory vessel 203. The entry points of the biomass particles and reactant gas into the cavity occurs at two or more entry locations at or near the top of the refractory vessel 203 and above the internally heated radiant tubes 206.

The one or more SiC radiant tubes 206 are used for radiant heat transfer to the biomass particles in the annular shaped cavity space, refractory lining of the vessel, and to the other radiant tubes 106, which can also re-radiate heat to particles. The feed lines 212 for the biomass and steam enter in multiple entry points in the upper portion of vessel. The natural gas fired regenerative burners 208 connects to one end of the tube to supply heated gases and flames to the two or more SiC radiant tubes 206. Merely one set of regenerative burners 208 connects to the tubes 206, at one end. Each tube 206 has an inner shell that directly connects to the gas fired regenerative burners 208, and the inner shell is surrounded by an external shell in which the flue gas flows, which has its heat extracted and radiated to the reactant gas and any particles entrained in the reactant gas. The multiple shell design of the internally heated SiC radiant tubes 206 has a more complex construction compared to simple straight radiant tubes. Multiple sets of tubes may have the multiple shell construction but one is shown for ease of illustration.

The refractory vessel 203 may be made of refractory lined steel. Note, differential expansion will not affect the seal between the SiC radiant tubes 206 and the refractory lined vessel 203 as much as in other designs. Syngas and ash product exit the bottom of the radiant heat chemical reactor 202.

The entrained-flow of chemical reactants into the chemical reactor 202 may start when the radiant heat driven chemical reactor 202 is at at least a minimum operational temperature of 750 degrees Celsius and preferably greater than 1000 degrees Celsius. The chemical reactor 202 can convert carbonaceous biomass materials into carbon monoxide and hydrogen by reacting the raw particles of biomass material with the steam for biomass gasification, and the steam with the supplemental methane for steam reforming at high temperatures, 700-1600 degrees C., with a controlled amount of steam, natural gas, and any combination, which then results in the gas mixture of synthesis gas.

The radiant tubes 206 and the refractory lining of the vessel 203 combine for radiant heat transfer to biomass particles in the annular cavity space at a significantly increased radiant heat transfer surface area compared to other designs, and maintain a higher temperature of radiant surface between 1100 to 1600 degrees C.

The control system controls the heating of the exothermic heat source 208 and a feed rate of chemical reactants into the chemical reactor through the one or more feed lines 212 to maintain the temperatures above 900° C. in order to cause a rapid gasification reaction of dispersed falling biomass particulates and reactant gas with potentially the heat-transfer-aid particles present to produce a resultant stable ash formation, complete amelioration of tar to less than 500 milligrams per normal cubic meter, and the production of the hydrogen and carbon monoxide products. The heating of each of the radiant tubes 206 may be controlled to operate independently or as a group of radiant tubes 206.

Without the control system getting rid of tar, substantial build up problems may occur. Excess steam or regular steam only cycles can also be introduced to get rid of sooting problems.

Tight seals 216 such as metal seals, welded seals, etc. are installed between the radiant tubes 206 that are internally heated and the refractory lined vessel 203. The tight seals are specifically designed to accommodate a differential thermal expansion of the radiant tubes 206 and the refractory lined vessel 203, which are potentially made out of different materials whose thermal expansion can affect the seal process at upper end temperatures. The radiant tubes 206 may have a 1400° C.-1800° C. surface temperature and the inner cavity of the refractory lined vessel 203 operates at temperatures between 900 C and 1600 C. Tight seals 216 may also be put onto the chemical reactant feed lines 212 or those feed lines entry points into the vessel may be part of the molded form of the vessel 203.

The chemical reactor 202 may have a variety of temperature sensors to measure inlet gas temperature, wall temperature, exit temperature, and any combination of these to provide feedback to the control system. The radiant heat chemical reactor 202 may be a single stage in which the chemical reaction occurs within the single vessel 203 of the chemical reactor 202.

Figure 3:
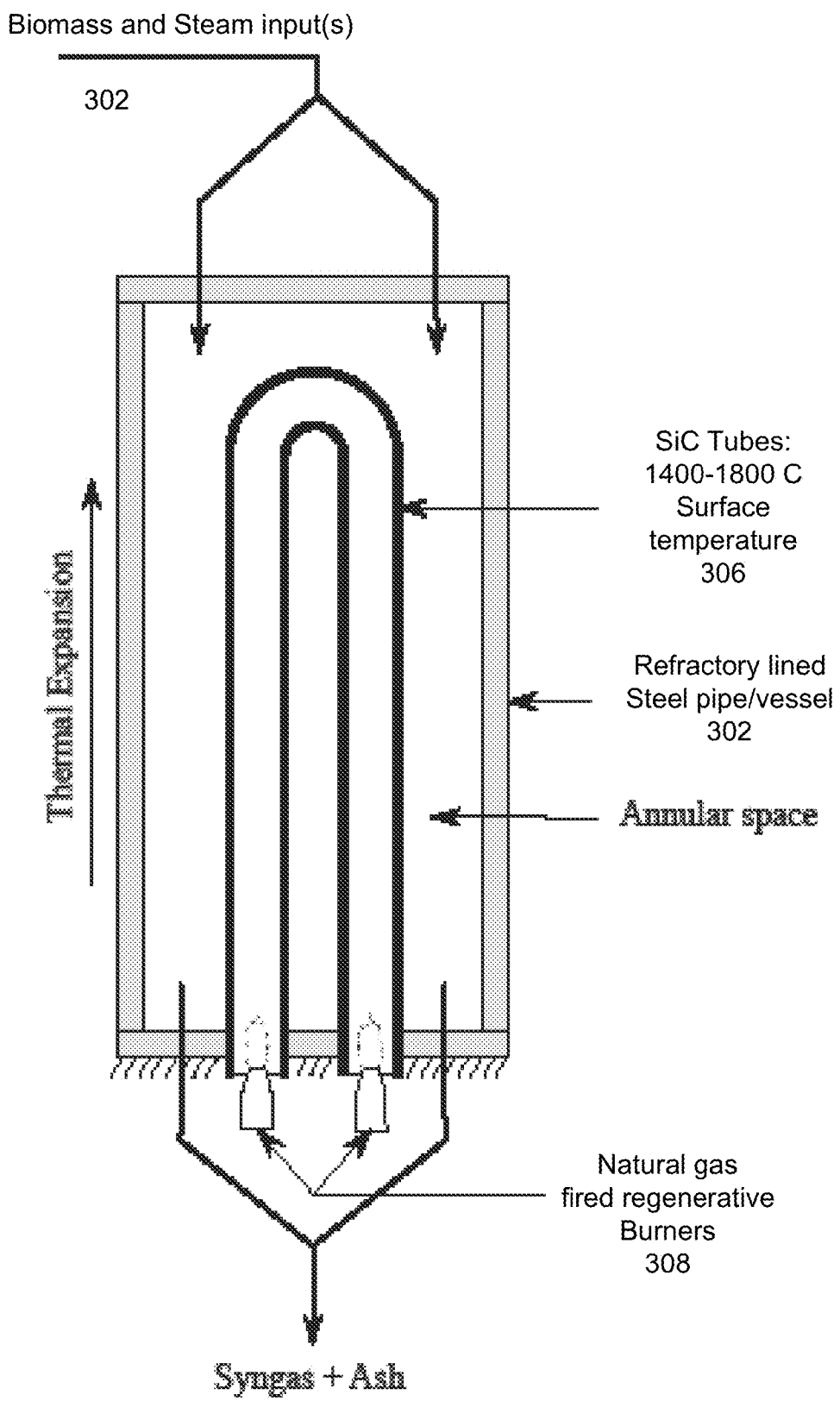
FIG. 3 illustrates a flow schematic of an embodiment for the radiant heat chemical reactor configured to generate chemical products including synthesis gas products.

FIG. 3 illustrates a flow schematic of an embodiment for the radiant heat chemical reactor configured to generate chemical products including synthesis gas products.

The internally heated radiant tubes 306 may be shaped in a non-straight geometry, such as U shaped. Multiple sets of tubes may be shaped in the non-straight geometry but one is shown for ease of illustration. Thus, the radiant tubes 306 that are shaped in a non-straight geometry may only contact and penetrate one end of the refractory lined vessel 302. Note, the differential expansion will not affect the seal between the SiC radiant tubes 306 and the refractory lined vessel 302 as much as in other designs. The single shell design of the non-straight geometry of the internally heated SiC radiant tubes 306 is simple to construct compared to multiple shell design, and also has a straightforward use of regenerative burners 308. The regenerative burners 308 connect to both ends of each radiant tube 306. Syngas and ash product exit the bottom end of the radiant heat chemical reactor 302, which also has the radiant tube 306 penetration/entry points.

Figure 4:
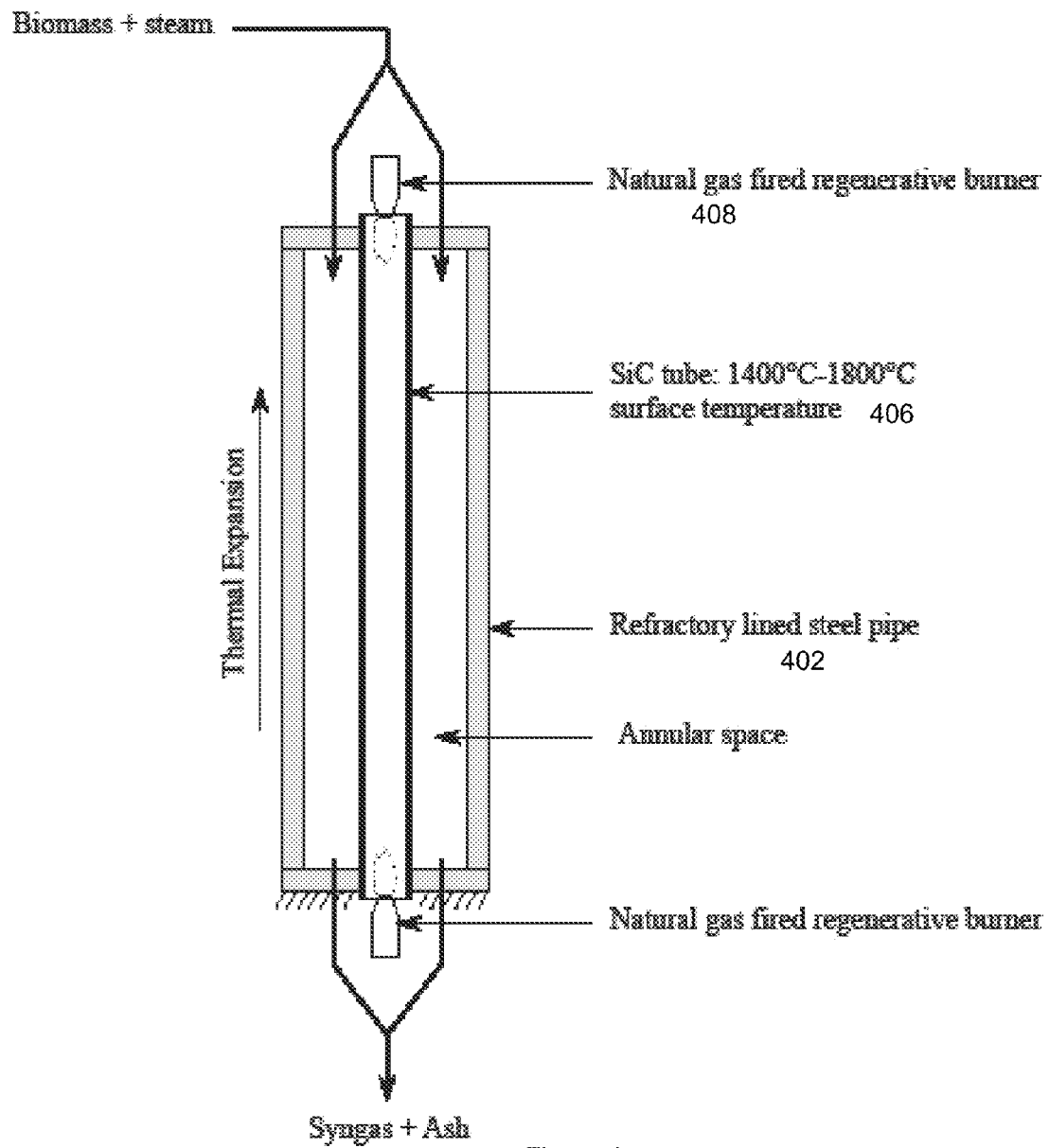
FIG. 4 illustrates a flow schematic of an embodiment for the radiant heat chemical reactor configured to generate chemical products including synthesis gas products.

FIG. 4 illustrates a flow schematic of an embodiment for the radiant heat chemical reactor configured to generate chemical products including synthesis gas products.

The feed lines 412 for the biomass and steam enter in at least two entry points at the top of the refractory vessel 403 into the annular shaped cavity space between the inner wall of the refractory vessel 403 and the radiant tubes 406. The refractory vessel 403 may made of a refractory lined steel pipe. Natural gas fired regenerative burners 408 at at least both ends may heat a single large diameter radiant tube.

Figure 5A:
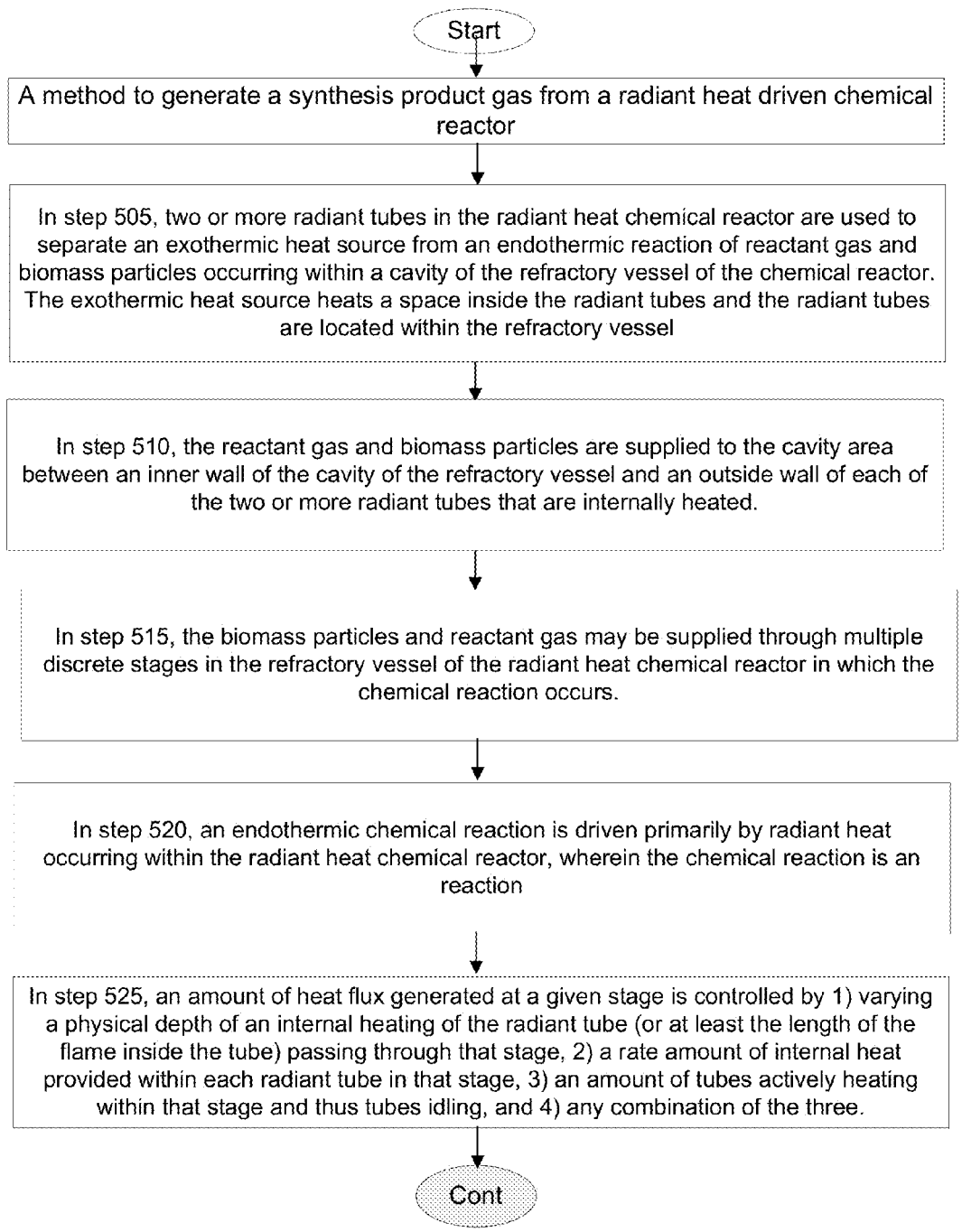

FIGS. 5a-5b illustrate a flow diagram of an embodiment for a method to generate a synthesis product gas from a radiant heat driven chemical reactor. Many methods are possible and change of sequential order of these steps. The following is an example.

In step 505, two or more radiant tubes in the radiant heat chemical reactor are used to separate an exothermic heat source from an endothermic reaction of reactant gas and biomass particles occurring within a cavity of the refractory vessel of the chemical reactor. The exothermic heat source heats a space inside the radiant tubes and the radiant tubes are located within the refractory vessel. A relatively small space within each given tube compared to an area within the cavity is used to efficiently heat the given tube to minimum threshold temperature and amount emitted radiant energy. The internally heated radiant tubes may be routed in a vertical orientation and enter at or near the top of the refractory vessel.

In step 510, the reactant gas and biomass particles are supplied to the cavity area between an inner wall of the cavity of the refractory vessel and an outside wall of each of the two or more radiant tubes that are internally heated. The biomass particles and reactant gas may be routed to enter the refractory vessel below the entry point of the internally heated/fired radiant tubes and at two or more entry locations at or near the top of the refractory vessel.

In step 515, the biomass particles and reactant gas may be supplied through multiple discrete stages in the refractory vessel of the radiant heat chemical reactor in which the chemical reaction occurs. Physical barrier surfaces in the refractory vessel increase residence time of the biomass particles and reactant gas within the refractory vessel by not just falling straight through the vessel and instead the internal geometry of the vessel defined by the physical barrier surfaces causes the biomass particles and reactant gas to travel a non-linear path through the vessel.

In step 520, a chemical reaction is driven primarily by radiant heat occurring within the radiant heat chemical reactor, wherein the chemical reaction is an endothermic reaction including one or more of biomass gasification ($CnHm+H_2O \rightarrow CO+H_2+H_2O+X$), steam methane reforming ($CH_4+H_2O \rightarrow CO+3H_2$), and steam methane cracking to produce ethane ($H_2O+CH_3+CH_3 \rightarrow C_2H_6+H_2O$); steam methane cracking to produce ethylene ($CH_4+H_2O \rightarrow C_2H_4$), and other similar reactions. By heating the radiant tubes with radiant energy (which re-radiate to the particles), the problem of generating heat from the exothermic reaction to drive the endothermic reaction (essentially the endothermic/exothermic balancing problem) is eliminated.

In step 525, an amount of heat flux generated at a given stage is controlled by 1) varying a physical depth of an internal heating of the radiant tube (or at least the length of the flame inside the tube) passing through that stage, 2) a rate amount of internal heat provided within each radiant tube in that stage, 3) an amount of tubes actively heating within that stage and thus tubes idling, and 4) any combination of the three.

In step 530, an amount of flames and heated gas from natural gas fired regenerative burners is supplied from at least both ends of the radiant tubes at temperatures between 900° C. and 1800° C.

In step 535, maintaining an environmental pressure within the refractory vessel with one or more tight seals made out of 1) metal or 2) a welded seal between the radiant tubes that are internally heated and the refractory lined vessel, where the tight seals are designed to accommodate a differential thermal expansion of the radiant tubes and the refractory lined vessel are potentially made out of different materials which can affect the seal process at upper end temperatures, and the radiant tubes have a 1400° C.-1800° C. surface temperatures and the vessel inner cavity operates at temperatures between 900 C and 1600 C. A very large cavity space is used compared to an area within a given tube and allow the large surface area to volume ratio of the particles flowing within the cavity to improve convection heat transfer from the radiant heat absorbing biomass and heat transfer aid particles to gas phase reactants.

In step 540, the heating of the exothermic heat source and a feed rate of chemical reactants into the cavity of the chemical reactor is controlled in order to maintain the temperatures above 900° C. in order to cause a rapid gasification reaction of dispersed falling biomass particulates and reactant gas to produce a resultant stable ash formation, complete amelioration of tar to less than 500 milligrams per normal cubic meter, and the production of the hydrogen and carbon monoxide products. Thus, synthesis product gases exit from the chemical reaction of the reactant gas and biomass particles from the radiant heat chemical reactor.

In step 545, a liquid fuel is generated from the synthesis product gases from the radiant heat chemical reactor.

Figure 6:
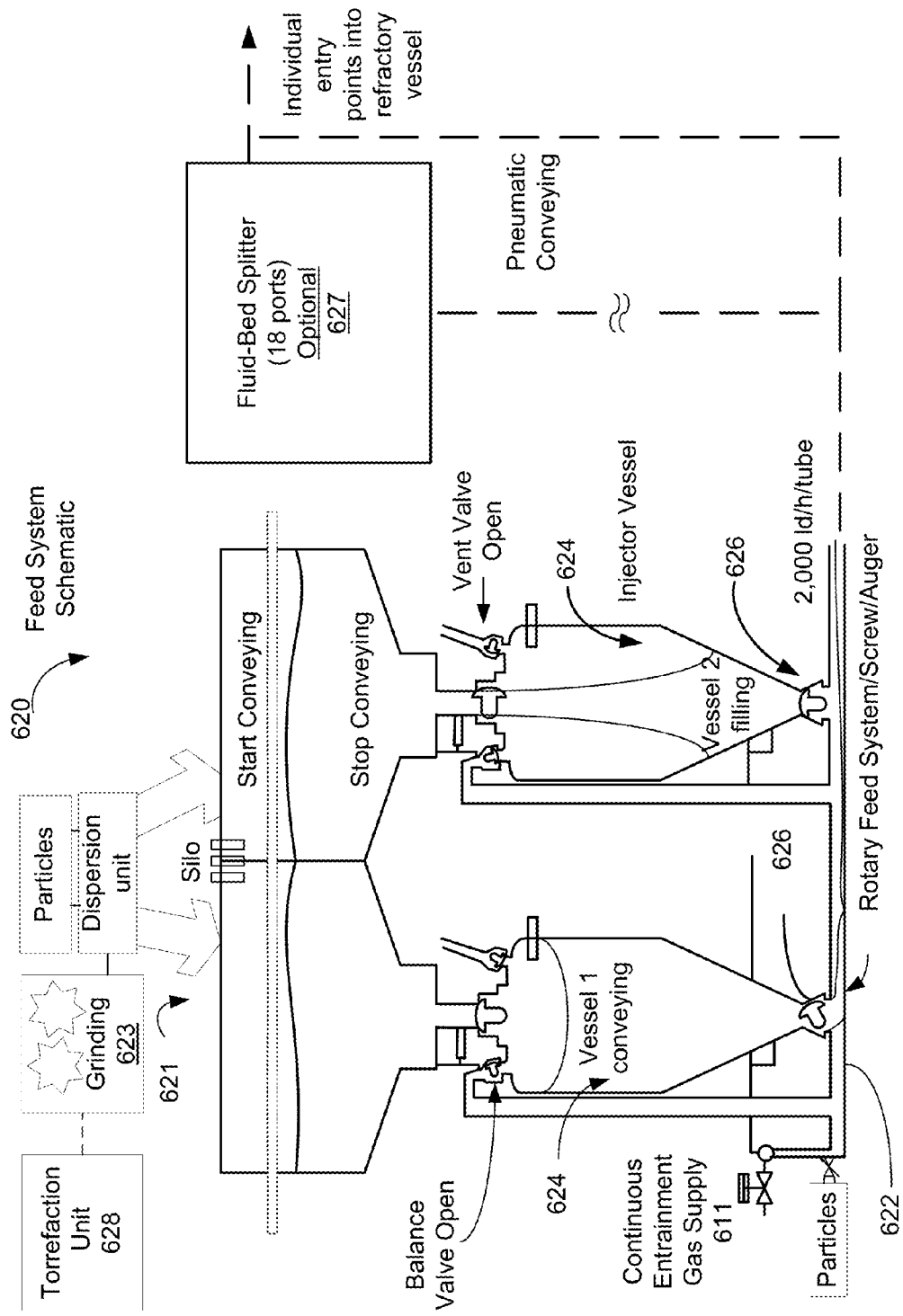
FIGS. 6 and 7 illustrate block diagrams of embodiments for an entrained-flow biomass feed system that supplies the biomass particles and heat-transfer-aid particles in a carrier gas to the chemical reactor.
Figure 7:
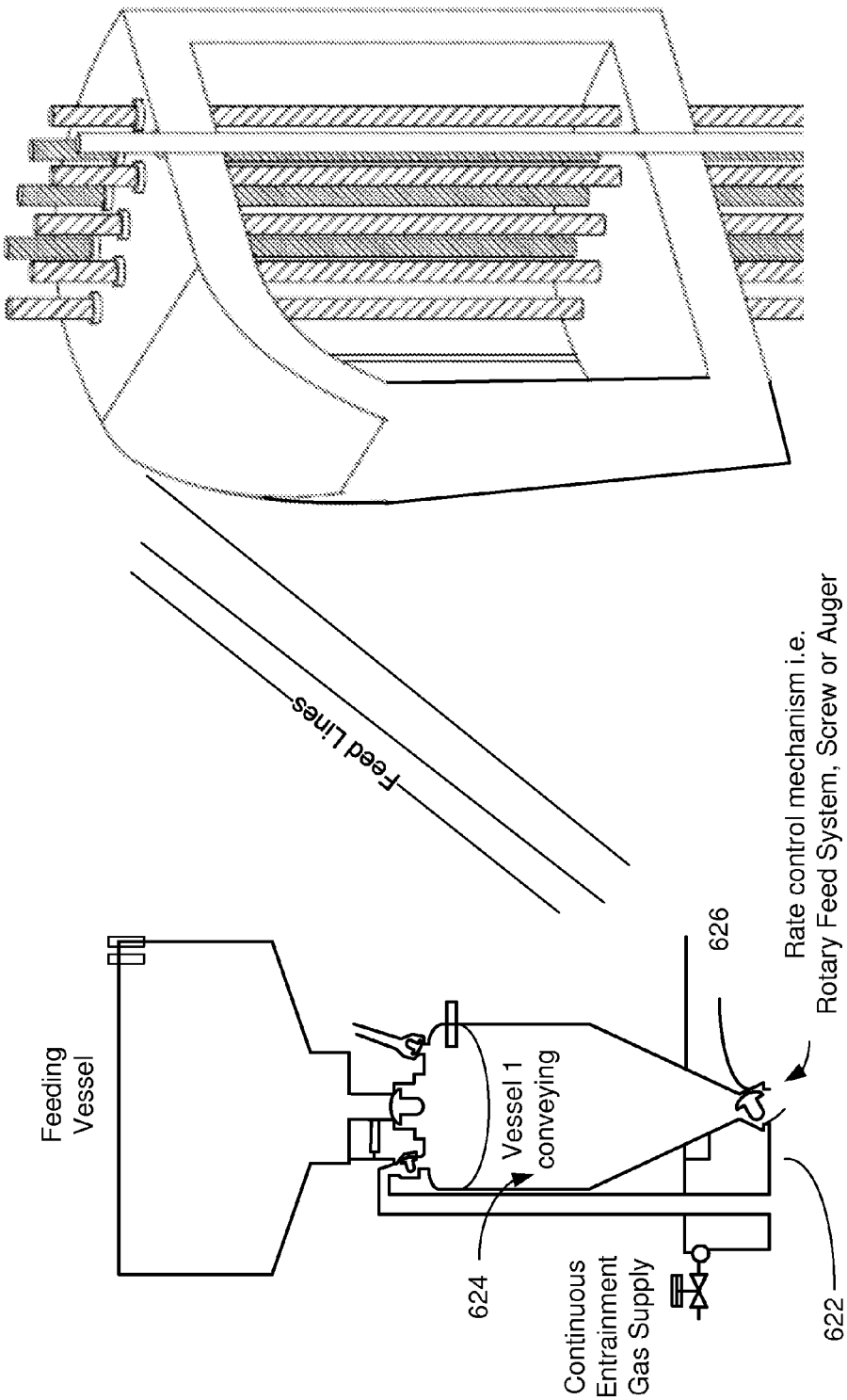

FIGS. 6 and 7 illustrate block diagrams of embodiments for an entrained-flow biomass feed system that supplies the biomass particles and heat-transfer-aid particles in a carrier gas to the chemical reactor. The entrained-flow biomass feed may go through a flow splitter 627 into the refractory vessel or directly go from a pressurized lock hopper pair 624 into the refractory vessel.

The entrained-flow biomass feed system 620 can include a pressurized lock hopper pair 624 that feeds the biomass to a rotating metering feed screw 622 and then into an entrainment gas pipe at the exit 626 of the lock hopper pair. The particles of the biomass are distributed into multiple entrainment gas lines by a flow splitter 627 to feed the two or more radiant tubes making up the chemical reactor.

In an embodiment, the high heat flux reactor and associated integrated system may also include the entrained-flow biomass feed system 620 having one or more lock-hopper pairs 624 equipped with a single multi-outlet feed splitter 627 that simultaneously feeds the particles of the biomass in pressurized entrainment gas lines into two or more tubes of the chemical reactor. The tubes may be controlled as discrete tube sets, each with two or more tubes. The gas source 611 may also supply pressurized entrainment gas in the form of recycled carbon dioxide from an amine acid gas removal step in the hydrocarbon fuel synthesis process, steam, or some other carrier gas. The multi-outlet feed splitter 627 provides and controls an amount of distribution of the particles of the biomass in the one or more pressurized entrainment gas lines that feed the two or more radiant tubes in the chemical reactor via allowing flow or no flow through a set of radiant tubes. Thus, each feeding vessel 624 of the biomass feed system supplies a feed splitter 627 that feeds, for example up to twelve radiant tubes in the chemical reactor. Each feeding vessel 624 has one or more outlets 626 configured to supply a consistent volumetric amount of biomass particles within ten percent of the demand signal amount when distributing biomass particles to the two or more radiant tubes.

The feed system may be configured to supply heat-transfer-aid particles and chemical reactants into the gasification reactor. The feed system may be configured to blend the biomass materials in the dispersion unit with the heat-transfer-aid particles prior to feeding and entraining them into the chemical reactor. The feed system may be configured to blend the heat-transfer-aid particles with the reactant gas in the entrainment gas lines as well.

The heat-transfer-aid particles may be mechanically metered and feed that parameter to the control system. The heat-transfer-aid particles are then entrained into the reactant gas flow that is then fed downward through the chemical reactor, which is vertically aligned. A separator coupled to the chemical reactor mechanically separates the heat-transfer-aid particles from the product gas stream and recovers these heat-transfer-aid particles for reuse as feedstock in the feeder system to the chemical reactor.

The recycled ash from the separator in the syngas clean up section is blended with biomass particles in the feed system to generate additional heat from both any remaining combustion and as a radiation absorption particle in order to fully utilize the remaining carbon atoms in the ash.

The high heat flux reactor and associated integrated system may also include a grinding system 623. The grinding system 623 has a grinding device that is at least one of 1) a mechanical cutting device, 2) a shearing device, 3) a pulverizing device, and 4) any combination of these that breaks apart the biomass, and a series perforated filters in the entrained-flow biomass feed system. The grinding device and perforated filters grind the partially pyrolyzed biomass from the torrefaction unit 628 to control the particle size of the biomass to be between 10 um and 1000 um. The torrefaction unit 628 is geographically located on the same site as the radiant heat driven chemical reactor and configured to be subject the biomass to partial pyrolysis with recouped waste heat from the chemical reaction in a temperature range of up to 300 degrees C. to make the biomass 1) brittle and easier for grinding, 2) dryer, less sticky, and easier to feed in a conveying system, 3) subject to less spoilage issues in storage as a torrefied biomass, as well as 4) produce off gases from the torrefaction process. The torrefaction unit 628 supplies partially pyrolyzed biomass to the grinding system 623. The torrefaction of the partially pyrolyzed biomass reduces the energy required by the grinding device to grind the biomass to the controlled particle size between 10 um and 1000 um. The off gases from the torrefaction of the biomass can be used for one or more of the 1) entrainment carrier gas, 2) an energy source for steam generation, 3) direct blending with the product gasoline, 4) a gas for the gas-fired regenerative burners or steam boilers, and 5) any combination of these.

The feedstock flexibility of being able to use multiple types of biomass without redesigning the feed and reactor process clearly gives an economic advantage over processes that are limited to one or a few available feed stocks.

Figure 8:
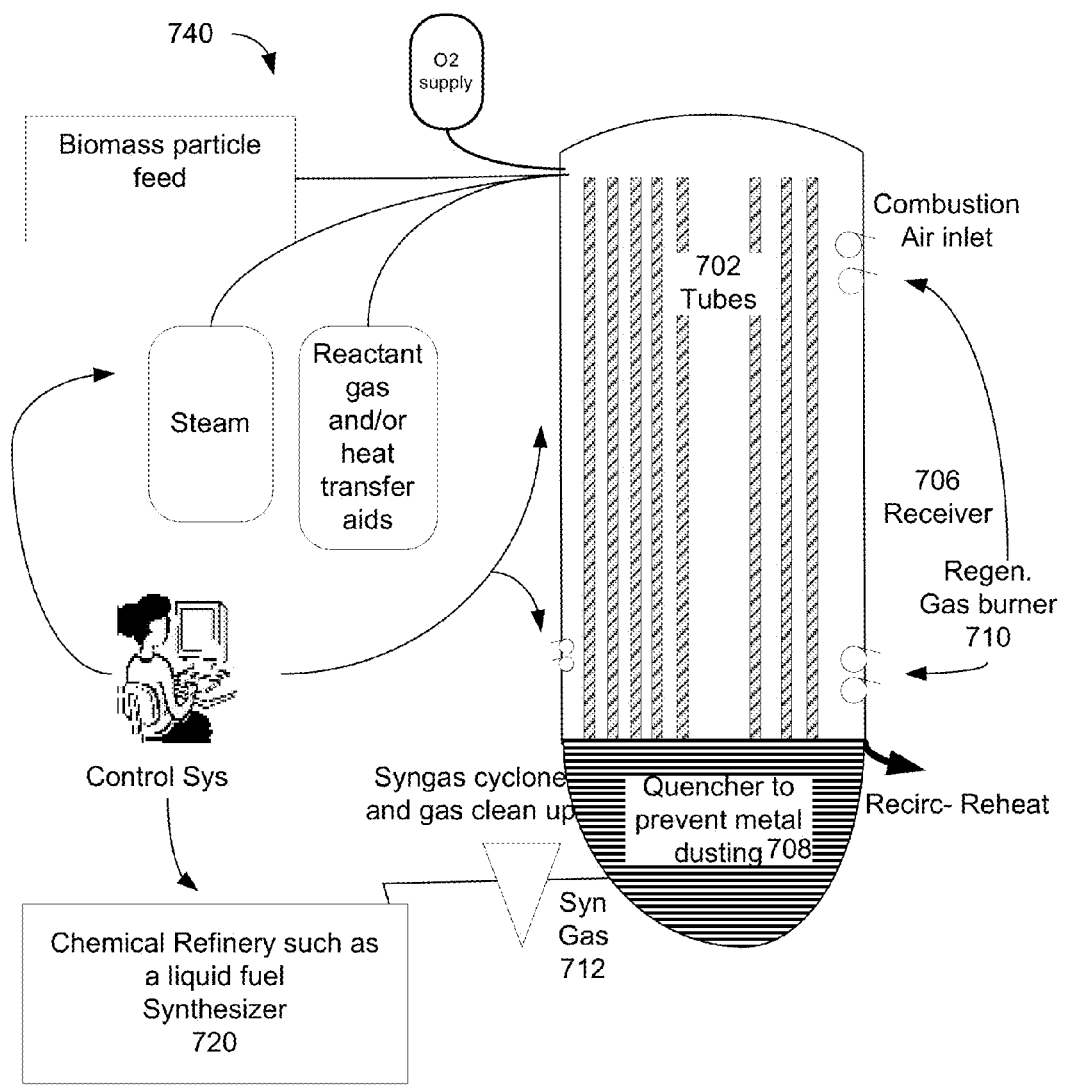
FIG. 8 illustrates a diagram of an embodiment of the radiant heat driven bio-refinery with multiple control systems that interact with each other.

FIG. 8 illustrates a diagram of an embodiment of the radiant heat driven bio-refinery with multiple control systems that interact with each other. In such a system, radiant heat energy may be provided to the chemical reactor 702. In this example, the chemical reactor may be heated by two or more sets of the gas-fired regenerative burners 710.

An entrainment carrier gas system supplies carrier gas for the particles of biomass in the feed system to the chemical reactor. The other chemical reactants, heat transfer aid particles, oxygen, and/or steam may also be delivered to the radiant tubes. As illustrated, chemical reactants, including biomass particles, may flow into the chemical reactor 702 and syngas flows out 712. The quench unit 708 may be used to rapidly cool the reaction products and prevent a back reaction into larger molecules.

The computerized control system may be multiple control systems that interact with each other. The computerized control system is configured to send a feed demand signal to feed system's to control an amount of 1) radiant tube sets to be fed particles of biomass in the chemical reactor, 2) amount of gas fired regenerative burners supplying heat, 3) rate at which particular gas fired regenerative burners supply heat, and 4) any combination of these based on control signals and the temperature measured for the chemical reactor. The control system may rely on feedback parameters including temperature of the reactor as well as feed forward parameters including anticipated changes in heat in from the burners and heat out from changes in an amount of chemical reactants and carrier gas being passed through the radiant tubes 702.

In general, the high heat transfer rates of the radiant tubes and cavity walls maintained by the control system allow the particles of biomass to achieve a high enough temperature necessary for substantial tar destruction and gasification of greater than 90 percent of the biomass particles into reaction products including the hydrogen and carbon monoxide gas in a very short residence time between a range of 0.01 and 5 seconds.

The control system keeps the reaction temperature in the chemical reactor high enough based on temperature sensor feedback to the control system to avoid the need for any catalyst to cause the chemical reaction occurring within the chemical reactor but allowing the temperature at or near the exit to be low enough for a hygiene agent supply line to inject hygiene agents to clean up the resultant product gas by removing undesirable compositions from the resultant product gas, promote additional reactions to improve yield, and any combination of these two, all while keeping the exit temperature of the chemical reactor greater than 900 degree C. to avoid tar formation in the products exiting the chemical reactor.

The control system may be configured to maintain the reaction temperature within the chemical reactor based upon feedback from a temperature sensor at at least 1200 degrees C. to eliminate the need for a catalyst for the chemical reactions as well as overdrive the endothermic reactions including the steam methane reforming and the steam ethane reforming, which are equilibrium limited; and thereby improve the equilibrium performance for the same amount of moles of reactant feedstock, to increase both yield of resultant gaseous products and throughput of that reactant feedstock.

The control system may control the multiple radiant tubes via splitting operation of them into two or more groups of tube subsets. The control system can do both for the integrated plant 1) control the feed to match the amount of energy, as well as control the radiant energy to match the amount of feed, now that system has the ability to control the amount of energy/heat sink out via increase or decrease amount of carrier gas and reactant flowing in a given set of radiant tubes as well as control heat into the reactor by 1) controlling an amount of fuel gas flowing in a given set of regenerative burners, 2) starting up additional sets of regenerative burners inside the thermal refractory vessel, or any combination of these.

The control systems of the reactor and liquid fuel plant 720, such as a Methanol to Gasoline synthesis plant, may have bi-directional communications between the chemical reactor and the liquid fuel plant, such as a methanol plant. For example, when a subset of tubes needs to be adjusted out for maintenance or due to a failure, then the integrated plant can continue to operate with increase biomass and entrainment gas flow through the chemical reactor to keep a steady production of syngas for conversion into a liquid fuel. Changing entrainment gas pressure in the radiant tubes can also be used to increase/decrease the heat sink effect of the biomass and gas passing through the tubes.

The integrated chemical plant 720 converts the supplied chemical reactants, such as particles of biomass, into gasoline in the integrated chemical plant as follows. The hydrogen and carbon monoxide products from the chemical reactor are converted in an on-site methanol synthesis plant to methanol, and the methanol from the methanol synthesis plant is converted to gasoline in a methanol-to-gas process. The on-site chemical synthesis reactor, such as a methanol synthesis plant, is geographically located on the same site as the chemical reactor and integrated to receive the hydrogen and carbon monoxide products in the form of syngas. The on-site chemical synthesis reactor has an input to receive the syngas, which contains the hydrogen and carbon monoxide products from the chemical reactor, and then is configured to use the syngas in a hydrocarbon synthesis process to create a liquid hydrocarbon fuel or other chemical. The methanol production from syngas production is decoupled from being directly tied the momentary rate of syngas production by storing excess syngas, supplying supplemental syngas, or idling methanol reactors.

Next, the various algorithms and processes for the control system may be described in the general context of computer-executable instructions, such as program modules, being executed by a computer. Generally, program modules include routines, programs, objects, components, data structures, etc. that perform particular tasks or implement particular abstract data types. Those skilled in the art can implement the description and/or figures herein as computer-executable instructions, which can be embodied on any form of computer readable media discussed below. In general, the program modules may be implemented as software instructions, Logic blocks of electronic hardware, and a combination of both. The software portion may be stored on a machine-readable medium and written in any number of programming languages such as Java, C++, C, etc. The machine-readable medium may be a hard drive, external drive, DRAM, Tape Drives, memory sticks, etc. Therefore, the component parts, such as the transaction manager, etc. may be fabricated exclusively of hardware logic, hardware logic interacting with software, or solely software.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms may be written in a number of different software programming languages. Also, an algorithm may be implemented with lines of code in software, configured logic gates in electronic circuitry, or a combination of both.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers, or other such information storage, transmission or display devices.

Figure 9:
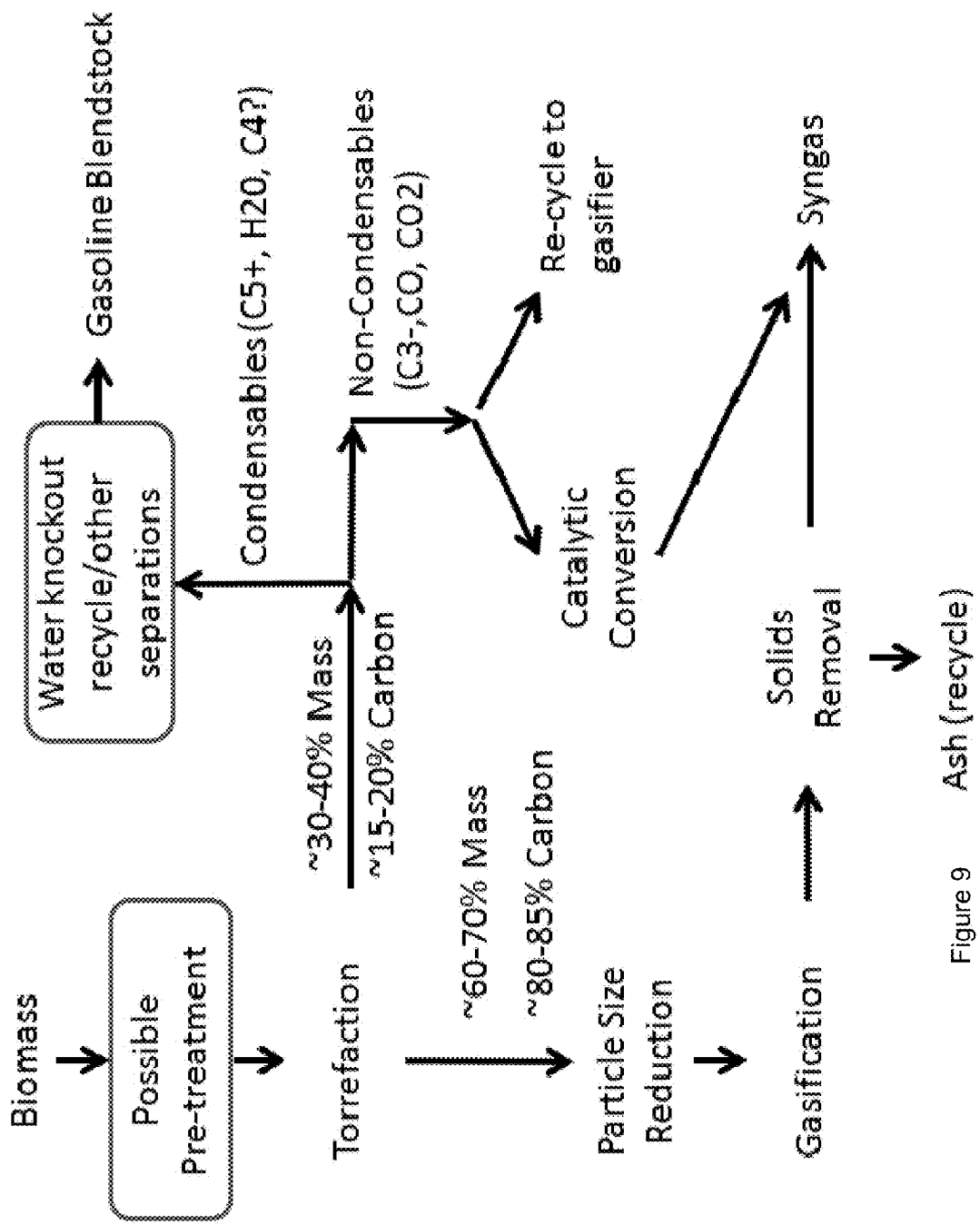
FIG. 9 illustrates a block diagram of an embodiment of another radiant heat driven chemical reactor that can utilize the internally heated radiant tubes.

FIG. 9 illustrates a block diagram of an embodiment of another radiant heat driven chemical reactor that can utilize the internally heated radiant tubes.

The source of the radiant heat maybe one or more of solar energy, gas-fired regenerative burners, nuclear power, and electric heaters, and any combination of these.

A refractory material may be one that retains its strength at high temperatures such as the oxides of aluminum (alumina), silicon (silica) and magnesium (magnesia). ASTM C71 defines provides additional guidance that refractories are "materials having those chemical and physical properties that make them applicable for structures, or as components of systems, that are exposed to environments above 538° C."

While some specific embodiments of the invention have been shown the invention is not to be limited to these embodiments. For example, the recuperated waste heat from various plant processes can be used to pre-heat combustion air, or can be used for other similar heating means. Regenerative gas burners or conventional burners can be used as a heat source for the furnace. The high flux reactor can be used for any type of endothermic reaction in any aspect of the chemical industry discussed herein. Biomass gasifier reactors other than a radiant heat chemical reactor may be used. The Steam Methane Reforming may be/include a SHR (steam hydrocarbon reformer) that cracks short-chained hydrocarbons (<C2O) including hydrocarbons (alkanes, alkenes, alkynes, aromatics, furans, phenols, carboxylic acids, ketones, aldehydes, ethers, etc., as well as oxygenates into syngas components. The invention is to be understood as not limited by the specific embodiments described herein, but only by scope of the appended claims.

The invention claimed is:

1. An apparatus, comprising:
a radiant heat chemical reactor is configured to generate chemical products including synthesis gas products;
two or more radiant tubes in the radiant heat chemical reactor configured to separate 1) an exothermic heat source from 2) an endothermic reaction of reactant gas and biomass particles occurring within a cavity of a refractory vessel of the chemical reactor, where the exothermic heat source heats a space inside the radiant tubes and the radiant tubes are located within the refractory vessel;
one or more feed lines are configured to supply the biomass particles entrained in the reactant gas to the cavity area between an inner wall of the cavity of the refractory vessel and an outside wall of each of the two or more radiant tubes that are internally heated;
one or more natural gas fired burners acting as the exothermic heat source and connect to both ends of the radiant tubes to supply heated gases and flames to the tubes.

2. The apparatus of claim 1, wherein the two or more internally heated radiant tubes are vertically orientated and have entry points near a top of the refractory vessel, where entry of the biomass particles and reactant gas for a biomass gasification reaction into the cavity occurs at two or more entry locations near the top of the refractory vessel, and where the refractory vessel is refractory lined, and where a first natural gas fired burner acting as the exothermic heat source connects to one end of a first tube to supply heated gases and flames to a first tube of the two or more radiant tubes, and each tube has an inner shell that directly connects to its gas fired burner, and the inner shell has its heat extracted and radiated to the reactant gas and any particles entrained in the reactant gas.

3. The apparatus of claim 1,
wherein at least two or more sets of burners connect to the tubes, with at least one set of burners per end.

4. The apparatus of claim 3, where the radiant tubes are made of ceramic or coated with ceramic and have entry points at both a top and bottom of the refractory vessel, where flames and heated gas of one or more natural gas fired burners are supplied to the multiple radiant tubes at temperatures between 900° C. and 1800° C., and a liquid fuel synthesis plant is configured to generate a liquid fuel from the synthesis product gases produced out of the chemical reactor.

5. An apparatus, comprising:
a radiant heat chemical reactor configured to generate chemical products including synthesis gas products, the radiant heat chemical reactor has two or more radiant tubes made out of a solid material and are located inside a cavity of a refractory vessel, where a chemical reaction driven by radiant heat occurs within an inner wall of a cavity of the refractory vessel and an outer wall of each of the one or more radiant tubes, wherein the chemical reaction is an endothermic reaction including one or more of 1) biomass gasification (CxHyOz+(x−z) H2O→xCO+(y/2+(x−z))H2), and 2) hydrocarbon reforming or cracking, including, but not limited to, steam methane reforming (CH4+H2O→CO+3H2), steam methane cracking to produce ethane (H2O+CH$_3$+ CH$_3$→C$_2$H$_6$+H2O), steam carbon gasification (C+H2O→CO+H2), and steam ethane cracking to produce ethylene (C2H6→C$_2$H$_4$+H2), to be conducted in the radiant heat chemical reactor using the radiant heat;
one or more feed lines are configured to supply chemical reactants including any of 1) biomass particles, 2) reactant gas, 3) steam, 4) chemically inert heat transfer aid particles, or 5) any of the four into the radiant heat chemical reactor, wherein an indirect radiation driven geometry of the radiant heat chemical reactor uses radiation as a primary mode of heat transfer the reactant gas and any particles entrained with the reactant gas, where each radiant tube separates an exothermic heat source from an endothermic reaction of the reactant gas occurring within the cavity of the refractory vessel, where the exothermic heat source heats a space inside the radiant tubes, where the one or more feed lines supply the chemical reactants for the chemical reaction to the cavity area between the inner wall of the cavity of the refractory lined vessel and the one or more radiant tubes that are internally heated, where one or more natural gas fired burners acting as the exothermic heat source and connect to both ends of the radiant tubes to supply heated gases and flames to the tubes; and
where the radiation is absorbed by any chemically inert heat transfer aid particles when present and any biomass particles when present in the reactant gas, and the heat is then transferred by conduction to the reacting gas at temperatures between 900° C. and 1600° C.

6. The apparatus of claim 5, where the radiant tubes that are internally heated decrease tube failure issues because a heating gradient across a wall of a tube expands a solid material of the tube while a higher pressure environment within the refractory vessel compresses the wall of the tube, where an internal portion of a first radiant tube contains the higher temperature of the heating gradient and a lower pressure environment compared to an outer portion of the first radiant tube, and wherein the chemical reaction is the biomass gasification.

7. The apparatus of claim 5, wherein at least two or more sets of burners connect to the tubes, at least one set of burners per end;
where the radiant tubes are made of ceramic or are coated with ceramic, where flames and heated gas of one or more natural gas fired burners are supplied to the multiple radiant tubes at temperatures between 900° C. and 1800° C.

8. The apparatus of claim 6, wherein the one or more feed lines are configured to supply biomass particles and reactant gas into an upper portion of the chemical reactor, and the feed lines for the biomass and steam enter below entry points in the vessel for the radiant tubes that are internally heated, where the two or more radiant tubes significantly increases radiant heat transfer surface area from just one tube, and after transiting through the radiant heat chemical reactor, syngas and ash product exit near a bottom of the refractory vessel, and a control system is configured to maintain the temperature of the chemical reactor to be above 1200 degrees C. in order to eliminate methane and C2+ hydrocarbons from the products exiting the radiant heat chemical reactor.

9. The apparatus of claim 5, further comprising:
one or more natural gas fired burners acting as the exothermic heat source connect to both ends of the radiant tubes, where each tube is heated from the inside by the burners at each end of the tube and the tube is contained inside a refractory lined vessel and a relatively constant heat flux is maintained while the chemical reactant is introduced into the area between the tube and the inner wall of the refractory lined vessel.

10. The apparatus of claim 5, wherein the refractory vessel is aligned to 1) absorb and re-emit radiant energy, 2) highly reflect radiant energy, and 3) any combination of these, to maintain an operational temperature of the radiant heat chemical reactor, where the one or more radiant tubes are located inside the cavity of the refractory vessel, where particles of biomass are gasified in the presence of a steam (H2O) in the biomass gasification reaction, and where the radiant tubes and the refractory lining of the vessel combine for radiant heat transfer to biomass particles in the cavity space at a significantly increased radiant heat transfer surface area compared to other designs, and maintain a higher temperature of radiant surface between 1100-1600 degrees C., and where the internally heated ceramic or ceramic coated radiant tubes have more efficient heating to obtain the radiant emissions to maintain the higher temperature due to a significantly reduced heated volume inside the tube compared to an entire cavity space.

11. The apparatus of claim 6, wherein the two or more internally heated radiant tubes are vertically orientated and merely have entry points near the top of the refractory vessel, where entry of the biomass particles and reactant gas for the biomass gasification reaction into the cavity occurs at two or more entry locations near the top of the refractory vessel and above the internally heated radiant tubes, and where the refractory vessel is refractory lined steel, and where the radiant tube has a multiple shell design with the exothermic heat source supplying heat to an inner shell and flue gases and heat gas from the inner shell flow in the outer shell to cause additional radiant heat to be emitted.

12. The apparatus of claim 5, further comprising:
tight seals installed between the radiant tubes that are internally heated and the refractory lined vessel, where the tight seals are specifically designed to accommodate a differential thermal expansion of the radiant tubes and the refractory lined vessel, which are made out of different materials whose thermal expansion can affect the seal process at upper end temperatures, and the radiant tubes are designed to have a 1200° C.-1800° C. surface temperature and the inner cavity of the refractory lined vessel are designed to operate at temperatures between 900° C. and 1600° C.

13. The apparatus of claim 5, wherein the feed lines for the chemical reactants enter in multiple entry points in the upper portion of vessel, where the natural gas fired burners connect to one end of the tube to supply heated gases and flames to a first tube of the two or more SiC radiant tubes.

14. The apparatus of claim 5, wherein the chemical reaction is biomass gasification and a liquid fuel synthesis plant configured to generate a liquid fuel from the products of the chemical reaction produced out of the chemical reactor.

15. The apparatus of claim 5, further comprising:
a boiler steam supply to provide steam to the radiant heat chemical reactor to make up at least part of the reactant gas, where the endothermic reaction is a biomass gasification reaction;
where the radiant tubes are vertically orientated and have entry points near the top of the refractory vessel, and entry of the biomass particles and reactant gas into the cavity occurs also at two or more entry locations near the top of the refractory vessel, and a control system controls the heating of the exothermic heat source and a feed rate of chemical reactants into the chemical reactor through the one or more feed lines to maintain the temperatures above 900° C. in order to cause a rapid gasification reaction of dispersed falling biomass particulates and reactant gas to produce a resultant stable ash formation, complete amelioration of tar to less than 500 milligrams per normal cubic meter, and the production of the hydrogen and carbon monoxide products.

* * * * *